US009750413B2

(12) United States Patent
Sandusky et al.

(10) Patent No.: US 9,750,413 B2
(45) Date of Patent: Sep. 5, 2017

(54) MASSIVELY PARALLEL DIFFUSE OPTICAL TOMOGRAPHY

(71) Applicant: National Technology & Engineering Solutions of Sandia, LLC, Albuquerque, NM (US)

(72) Inventors: John V. Sandusky, Albuquerque, NM (US); Todd A. Pitts, Rio Rancho, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 326 days.

(21) Appl. No.: 14/045,056

(22) Filed: Oct. 3, 2013

(65) Prior Publication Data

US 2015/0313470 A1 Nov. 5, 2015

(51) Int. Cl.
*A61B 5/00* (2006.01)
(52) U.S. Cl.
CPC ................................ *A61B 5/0073* (2013.01)
(58) Field of Classification Search
None
See application file for complete search history.

(56) References Cited

U.S. PATENT DOCUMENTS

| 6,335,792 | B1* | 1/2002 | Tsuchiya | G01N 21/4795 356/343 |
| 7,495,748 | B1* | 2/2009 | Sandusky | G01C 3/08 356/5.1 |
| 2002/0057757 | A1* | 5/2002 | Khoury | G02B 21/0004 378/21 |
| 2004/0015062 | A1* | 1/2004 | Ntziachristos | A61B 5/0073 600/312 |
| 2006/0173354 | A1* | 8/2006 | Ntziachristos | A61B 5/0066 600/476 |
| 2010/0224782 | A1* | 9/2010 | Pan | A61B 5/0062 250/334 |

OTHER PUBLICATIONS

McBride, et al., "A Parallel-Detection Frequency-Domain Near-Infrared Tomography System for Hemoglobin Imaging of the Breast in Vivo", Review of Scientific Instruments, vol. 72, No. 3, Mar. 2001, pp. 1817-1824.

(Continued)

*Primary Examiner* — Long V Le
*Assistant Examiner* — Don N Ho
(74) *Attorney, Agent, or Firm* — Medley, Behrens & Lewis, LLC; Samantha Updegraff

(57) ABSTRACT

Diffuse optical tomography systems and methods are described herein. In a general embodiment, the diffuse optical tomography system comprises a plurality of sensor heads, the plurality of sensor heads comprising respective optical emitter systems and respective sensor systems. A sensor head in the plurality of sensors heads is caused to act as an illuminator, such that its optical emitter system transmits a transillumination beam towards a portion of a sample. Other sensor heads in the plurality of sensor heads act as observers, detecting portions of the transillumination beam that radiate from the sample in the fields of view of the respective sensory systems of the other sensor heads. Thus, sensor heads in the plurality of sensors heads generate sensor data in parallel.

11 Claims, 6 Drawing Sheets

(56) References Cited

OTHER PUBLICATIONS

Chen, et al., "Portable Near-Infrared Diffusive Light Imager for Breast Cancer Detection", Journal of Biomedical Optics, vol. 9, No. 3, May/Jun. 2004, pp. 504-510.
Wang, et al., "Multi-Channel Photon Counting DOT System Based on Digital Lock-in Detection Technique", Proc. of SPIE vol. 7896, 2011, pp. 1-10.
Choe, et al., "Differentiation of Benign and Malignant Breast Tumors in-vivo Three-Dimensional Parallel-Plate Diffuse Optical Tomography", Journal of Biomedical Optics, vol. 14, No. 2, Mar./Apr. 2009, pp. 1-18.
Lee, et al., "Transmission RF Diffuse Optical Tomography Instrument for Human Breast Imaging", Proc. of SPIE-OSA Biomedical Optics, vol. 6629, 2007, pp. 1-6.
Ban, et al., "Diffuse Optical Tomography in the Presence of a Chest Wall", Journal of Biomedical Optics, vol. 18, No. 2, Feb. 2013, pp. 1-11.
Erickson, et al., "Breast Cancer Imaging and Tomography Using a Hand-Held Optical Imager", Proc. of SPIE vol. 8214, 2012, pp. 1-9.
Flexman, et al., "Digital Optical Tomography System for Dynamic Breast Imaging", Journal of Biomedical Optics, vol. 16, No. 7, Jul. 2011, pp. 1-16.
Grable, et al., "Optical Computed Tomography for Imaging the Breast: First Look", Proceedings of SPIE vol. 4082, 2000, pp. 1-6.

\* cited by examiner

MASSIVELY PARALLEL DIFFUSE OPTICAL TOMOGRAPHY

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Scientific and clinical studies have relatively recently been performed with respect to diffuse optical tomography, which maps attenuation and scattering coefficients, which are then related to chemical processes which are known to alter such coefficients. Compared to x-ray tomography, which maps only the affective atomic density that attenuates x-ray transmission, diffuse optical tomography can be employed to map chemical structure when it is applied in spectral regions that are absorbed by chemical bonds.

Conventionally, diffuse optical tomography has been utilized in mammography systems. A conventional diffuse optical tomography for mammography system includes an annular fiber-optic probe array that comprises a plurality of optical fibers. In such a system, one optical fiber is placed in contact with a breast and caused to transmit an optical signal having a wavelength near the absorption resonance of hemoglobin (750-900 nm), while the other optical fibers in the fiber-optic probe array, also in contact with the breast, collect light exiting the breast and pass such light to photodetectors, which then produce a photocurrent. A lock-in amplifier is coupled to a single photodetector (associated with a single optical fiber from the "sensing" optical fibers), and measures the phase and amplitude of the photocurrent produced by the photo-detectors. Typically, only one lock-in amplifier is used in a conventional diffuse optical tomography for mammography system, as lock-in amplifiers tend to be relatively large in size and relatively expensive.

Since such a mammography system includes a single lock-in amplifier, photocurrent from the photo-detectors coupled to the sensing optical fibers must be read serially. Once the photocurrent from all of the photodetectors respectively associated with the sensing optical fibers have been read, one of the sensing optical fibers is caused to be the "illuminating" optical fiber to provide illumination, while the previous illuminating optical fiber becomes one of the sensing optical fibers. This process is repeated until at least half of the optical fibers have been selected to be the illuminating optical fiber. The set of photocurrent phase and amplitude measurements composes a tomogram at a particular wavelength at the particular plane through the breast at which the probe array is located.

Subsequently, the wavelength of illumination output by the optical fibers is altered to be within the hemoglobin absorption resonance, and the process described above is repeated such that a new tomogram is generated at the same plane of the breast. Typically, the transmission wavelength will be stepped through several values within and near the absorption resonance, thus developing a set of tomograms corresponding to the differing absorption properties of the breast tissue. By applying tomography inversion techniques, the measured phase and amplitude of the photocurrent can be processed to indicate the location of absorbers within the measurement plane. By sliding the annular fiber-optic probe array to a new position along the tissue, a complete set of tomograms can be obtained, finally yielding a three-dimensional plot of absorber density.

It can be ascertained that several deficiencies are associated with such a conventional mammography system. Specifically, computing a complete set of tomograms can take several minutes, as the annular fiber-optic array must be placed at multiple positions and the role of illuminating fiber-optic must be altered. During this time, natural patient motion such as respiration may disturb the registration of the fibers to the breast, resulting in blurred or erroneous tomographic reconstruction. Additionally, the annular fiber-optic array must be in contact with human tissue, which often can cause the patient discomfort and may bring forth hygiene concerns.

SUMMARY

The following is a brief summary of subject matter that is described in greater detail herein. This summary is not intended to be limiting as to the scope of the claims.

Described herein are various technologies pertaining to a diffuse optical tomography system that can acquire data massively in parallel. Further, the diffuse optical tomography technology described herein can be contactless, such that when used in a mammography application (or other procedure), sensors need not come into contact with a patient. The diffuse optical tomography system includes a plurality of sensor heads that can be positioned on respective different sides of a sample (e.g., a tissue volume). In an exemplary embodiment, the sample can be human tissue, such as breast tissue, brain tissue, bone tissue, etc. In other examples, the sample can be an explosive material, foam that coats circuit componentry, etc. Each sensor head in the plurality of sensor heads can include a respective optical emitter (e.g., a laser) and a respective sensor device (e.g., a focal plane array, a charged coupled device (CCD) array, a complementary metal-oxide-semiconductor (CMOS) array, etc.). Pursuant to an example, a first sensor head in the plurality of sensor heads can be configured to be an illuminating sensor head, such that a first optical emitter in the first sensor head emits an intensity-modulated transillumination signal to a first portion of the (translucent) sample. In an exemplary embodiment, the first optical emitter can be configured to simultaneously (or substantially simultaneously/within 5 or few seconds) emit transillumination beams having different respective wavelengths, wherein each of the transillumination beams is respectively intensity-modulated.

A computing apparatus that is in communication with the plurality of sensor heads can be configured to control operation of the plurality of sensor heads, wherein the computing apparatus can cause the first optical emitter of the first sensor head to emit the transillumination beam, while controlling the other sensor heads in the plurality of sensor heads to prevent their respective optical emitters from emitting optical signals. Instead, the computing apparatus can control the other sensor heads in the plurality of sensor heads to capture respective portions of the transillumination beam that radiate from the sample (e.g., translucent, semi-clear, or transparent sample) within the respective fields of views of the sensor heads. With more particularity, the transillumination beam emitted by the first optical emitter will diffuse through the sample, such that portions of the transillumination beam will exit the sample at different regions thereof. The sensor devices of the other sensor heads have respective fields of view and capture portions of the transillumination beam that radiate from the sample in their fields of view. A field of view, for instance, may be an entire side of the sample.

Values output by a sensor device are indicative of respective transmission phases of the respective portions of the transillumination beam and respective amplitudes of the respective portions of the transillumination beam that are captured by the sensor device in a plurality of pixels. After values have been read from all of the pixels of the sensor devices of the non-illuminating sensor heads, the first optical emitter in the first sensor head can be controlled to be directed towards a different location on the sample. The sensor devices of the non-illuminating sensor heads in the plurality of sensor heads again capture respective images of the sample in their respective fields of view, wherein values of pixels in the images are indicative of respective transmission phases of the respective portions of the transillumination beam and respective amplitudes of the respective portions of the transillumination beam at such pixels. This process can repeat until the first optical emitter has directed transillumination beams at desired locations in the sample.

Thereafter, the computing apparatus can control the plurality of sensor heads to cause a different one of the sensor heads to act as the illuminator, while controlling the other sensor heads to capture images of portions of transillumination beams emitted by the illuminator that radiate from the sample. This process repeats until each of the sensor heads has acted as the illuminator. The computing apparatus can receive the data output by the sensor devices of the plurality of sensor heads and can construct a volumetric image of the sample. In contrast to conventional diffuse optical tomography techniques, the volumetric image can be generated relatively quickly (e.g., less than two minutes) due to the massively parallel acquisition of illumination data.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
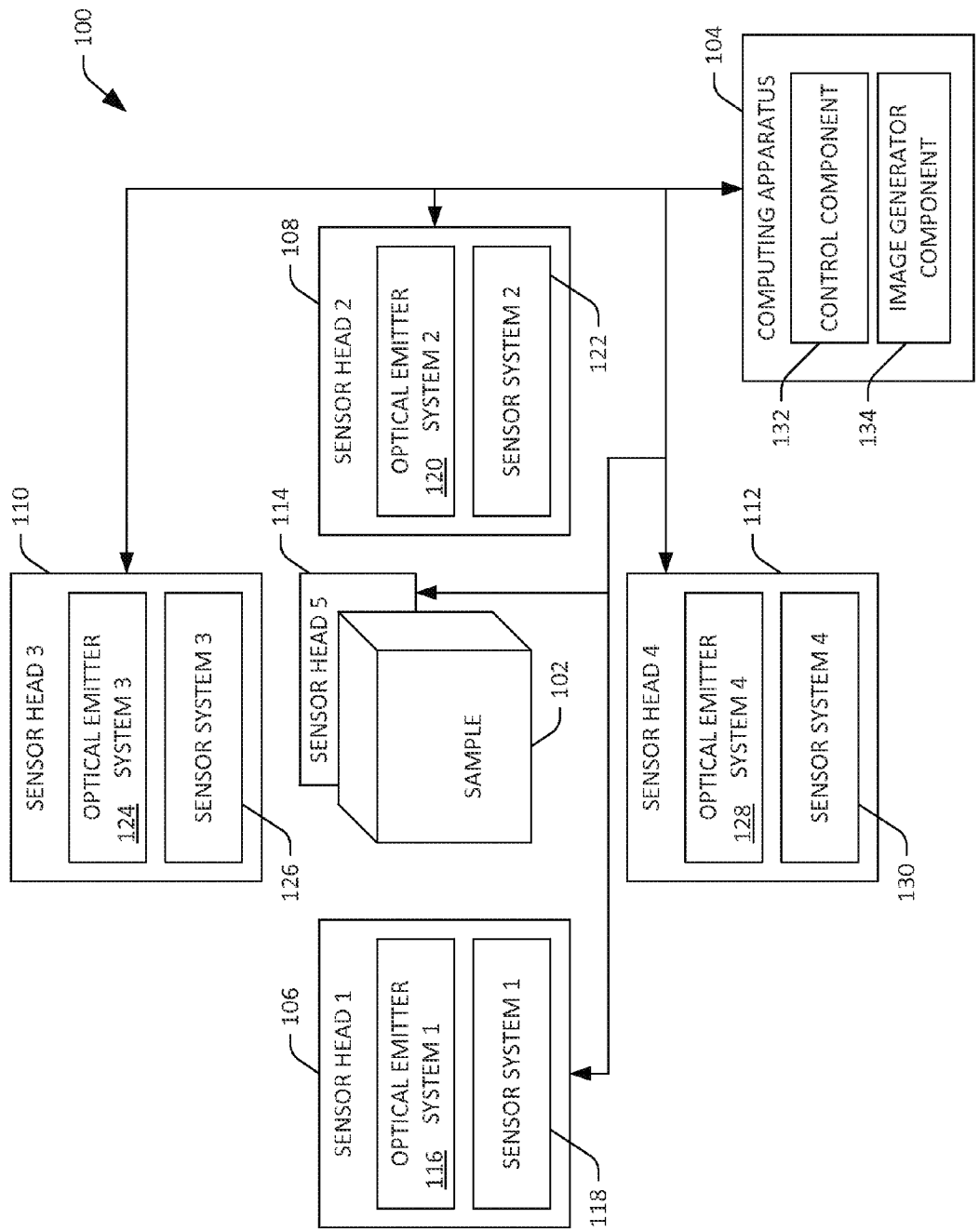
FIG. 1 is a functional block diagram of an exemplary diffuse optical tomography system that can be employed to generate a volumetric image of a sample.

Various technologies pertaining to diffuse optical tomography are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Additionally, as used herein, the term "exemplary" is intended to mean serving as an illustration or example of something, and is not intended to indicate a preference.

With reference now to FIG. 1, an exemplary diffuse optical tomography system 100 is illustrated. The diffuse optical tomography system 100 is configured to generate a volumetric image of a sample 102 (e.g., translucent, semi-clear, or transparent sample). In an exemplary embodiment, the sample 102 may be human tissue. For instance, the human tissue may be breast tissue, brain tissue, bone, etc. Accordingly, the diffuse optical tomography system 100 may be particularly well-suited for use as a mammography system, as a system for identifying/analyzing brain function (functional brain imagery), as a system for analyzing the effectiveness of medication relative to human joints, as a system for performing foam metrology (e.g., to detect or inspect objects embedded in foam, such as circuit board components, or to examine the foam for changes in structure or composition, such as may be due to aging, heating, chemical reaction, or exposure to radiation), etc. Further, the diffuse optical tomography system 100 may be particularly well-suited for analyzing and/or detecting explosives. With more particularity, the diffuse optical tomography system 100 can be configured to generate a volumetric mapping of water content, pressure, effects of ionizing radiation, and binder molecular weight in explosives, and further to distinguish differences in the volumetric density of explosives from binders, plasticers, and stabilizers. Further, the diffuse optical tomography system 100 is well-suited for inspecting high-voltage potting, since an absorption spectrum of high-voltage potting changes locally in the region where electrical breakdown has occurred. In a preferred embodiment, the sample 102 may be any suitable sample (e.g., translucent, semi-clear, or transparent sample); thus, the optical tomography system 100 can be employed with respect to many diffusely scattering materials that have spectral features in the ultraviolet to far infrared spectrum, and are associated with image demodulation techniques known in the art.

The structure of the diffuse optical tomography system 100 is now described. The diffuse optical tomography system 100 comprises a computing apparatus 104 that is configured to output power and/or control signals. The system 100 further comprises a plurality of sensor heads 106-114 that are in communication with the computing apparatus 104. Thus, the computing apparatus 104 can output control signals that are configured to control operation of the plurality of sensor heads 106-114, and can further receive data from the plurality of sensor heads 106-114. The plurality of sensor heads 106-114 can be positioned about different respective sides of the sample 102. Thus, for instance, as shown, the first sensor head 106 can be positioned relative to a first side of the sample 102 and a second sensor head 108 can be positioned on a second side of the sample 102, wherein the second side opposes the first side. Similarly, the third sensor head 110 can be positioned relative to a third side of the sample 102, while the fourth sensor head 112 can be positioned relative to a fourth side of the sample 102 that is opposite the third side of the sample 102 and orthogonal to the first and second sides of the sample 102. The fifth sensor head 114 can be positioned relative to a fifth side of the sample 102.

While the diffuse optical tomography system 100 is illustrated as comprising five sensor heads, it is to be understood that the system 100 may include more or fewer sensor heads. For instance, if the diffuse optical tomography system 100 is utilized as a mammography system, the exemplary system 100 may not include the first sensor head 106. Instead, an opaque barrier may be positioned on the first side of the sample 102 to isolate the sample 102 from other human tissue. In such an embodiment, the second sensor head 108 may be a lateromedial sensor head, the third sensor head 110 may be a craniocaudal sensor head, the fourth sensor head 112 may be a caudocranial sensor head, and the fifth sensor head 114 may be an anteroposterior sensor head.

Each sensor head in the plurality of sensor heads 106-114 comprises a respective optical emitter system and a respective sensor system. As will be described in greater detail below, each sensor head in the plurality of sensor heads 106-114 may optionally include multiple optical emitter systems that are configured to simultaneously (or substantially simultaneously/within 5 or few seconds) emit respective beams at differing wavelengths.

In the exemplary system 100 shown in FIG. 1, the first sensor head 106 includes a first optical emitter system 116 and a first sensor system 118; the second sensor head 108 includes a second optical emitter system 120 and a second sensor system 122; the third sensor head 110 includes a third optical emitter system 124 and a third sensor system 126; the fourth sensor head 112 includes a fourth optical emitter system 128 and a fourth sensor system 130; and the fifth sensor head 114 includes a fifth optical emitter system (not shown) and a fifth sensor system (not shown). The optical emitter systems of the sensor heads 106-114 are positioned relative to the sample 102 such that beams output thereby are directed towards the sample 102 and diffuse therethrough. The sensor systems of the sensor heads 106-114 are positioned relative to the sample 102 to detect illumination radiating from the sample 102. Thus, the optical emitter systems are configured to emit transillumination beams towards the sample 102, and the sensor systems are configured to output electrical signals that are indicative of transmission phase and amplitude of light exiting the sample 102 at respective portions of the sample 102 in the respective fields of view of the sensor heads 106-114.

Operation of the diffuse optical tomography system 100 is now described. The computing apparatus 104 comprises a control component 132 that is configured to output control signals to the plurality of sensor heads 106-114. In general, the control component 132 transmits a control signal to one sensor head that causes the sensor head to act as an illuminator, such that its optical emitter system scans an intensity-modulated transillumination beam in a pattern on one side of the sample 102. The control component 132 transmits control signals to the other sensor heads in the system 100 that cause such sensor heads to act as observers, such that their respective sensor devices capture and demodulate radiant images of the sample 102. The control component 132 then causes the roles of transillumination and observation to be switched amongst the plurality of sensor heads 106-114 until a complete set of data is obtained.

In an exemplary embodiment, each optical emitter system in the plurality of sensor heads 106-114 can be configured to emit transillumination beams having wavelengths that are at, as well as proximate to, an absorption wavelength of a chemical of interest. For instance, the absorption wavelength of hemoglobin is 750-900 nm. Accordingly, each optical emitter system in the plurality of sensor heads 106-114 can be configured to emit a respective transillumination beam having a wavelength below 750 nm, a transillumination beam having a wavelength between 750 and 900 nm, and a transillumination beam having wavelength that is above 900 nm. Further, each optical emitter system in the plurality of sensor heads 106-114 can be configured to emit respective polyspectral transillumination beams having simultaneous discrete spectral lines within and near the absorption resonance of the chemical of interest. An exemplary technique for emitting polyspectral transillumination beams is set forth in U.S. Pat. No. 7,495,748, the entirety of which is incorporated herein by reference. In such an embodiment, the sensor systems of the sensor heads 106-114 can detect modulation amplitude and phase measurements simultaneously at the predefined set of transillumination wavelengths. Such techniques are also described in U.S. Pat. No. 7,495, 748.

In another exemplary embodiment, the optical emitter systems of the sensor heads 106-114 can be configured to output a transillumination beam with a single wavelength at any given point in time. In such an embodiment, an optical emitter system can serially generate transillumination beams of different wavelengths. Thus, for instance, the control component 132 can cause the first sensor head 106 to act as the illuminator, and can further cause the optical emitter system 116 of the first sensor head 132 to initially emit a first transillumination beam having a first wavelength. While the optical emitter system 116 is outputting the first transillumination beam, the control component 132 can control the sensor systems of the sensor heads 108-114 to output amplitude and phase measurements for the first transillumination beam. Thereafter, the control component 132 can control the first optical emitter system 116 to output a second transillumination beam having a second wavelength, while controlling the sensory systems of the observer sensor heads to output amplitude and phase measurements for the second transillumination beam. Such process can continue until transillumination beams with desired wavelengths have been emitted by the first optical emitter system 116.

The computing apparatus 104 additionally includes an image generator component 134 that receives amplitude and phase measurements output by the sensor systems of the sensor heads 106-114. The image generator component 134 can then generate a volumetric image of the sample 102 based upon such measurements. The volumetric image can be indicative of location of the chemical of interest in the sample 102.

The diffuse optical tomography system 100 exhibits numerous advantages over conventional diffuse optical tomography systems. For example, the system 100 is contactless, such that the sensor heads 106-114, regardless as to whether they are acting as illuminators are observers, do not contact the sample 102. For instance, in a mammography application, the diffuse optical tomography system 100 is associated with improved patient comfort and hygiene compared to conventional diffuse optical tomography systems, as the sensor heads 106-114 need not come into contact with the breast of the patient. Further, as indicated above, the sensor systems of the sensor heads 106-114 can include focal plane arrays. Accordingly, sampling density of the sample 102 corresponds to a pixel count on a focal plane array, which may be tens, hundreds, or thousands of megapixels. For instance, 100 megapixels on a diameter of the sample 102 of 4 inches may produce a sampling interval of the sample 102 as small as 30 µm, which is an improvement in resolution of a factor of one hundred over conventional fiber-optic probe tips, whose typical sampling interval is on the order of 3 mm.

Additionally, as mentioned above, the sensor heads 106-114 may include multiple optical emitter systems. In an exemplary embodiment, as will be described in greater detail below, the sensor heads 106-114 can be configured to construct a three-dimensional model of the surface of the sample 102 prior to generating the volumetric image of the sample 102. This can be accomplished by causing optical emitter systems of the sensor heads 106-114 to emit flood illumination beams, and configure the sensor systems to output measurements pertaining to phase and amplitude of light that reflects from the sample 102 (rather than diffusing through the sample 102).

Figure 2:
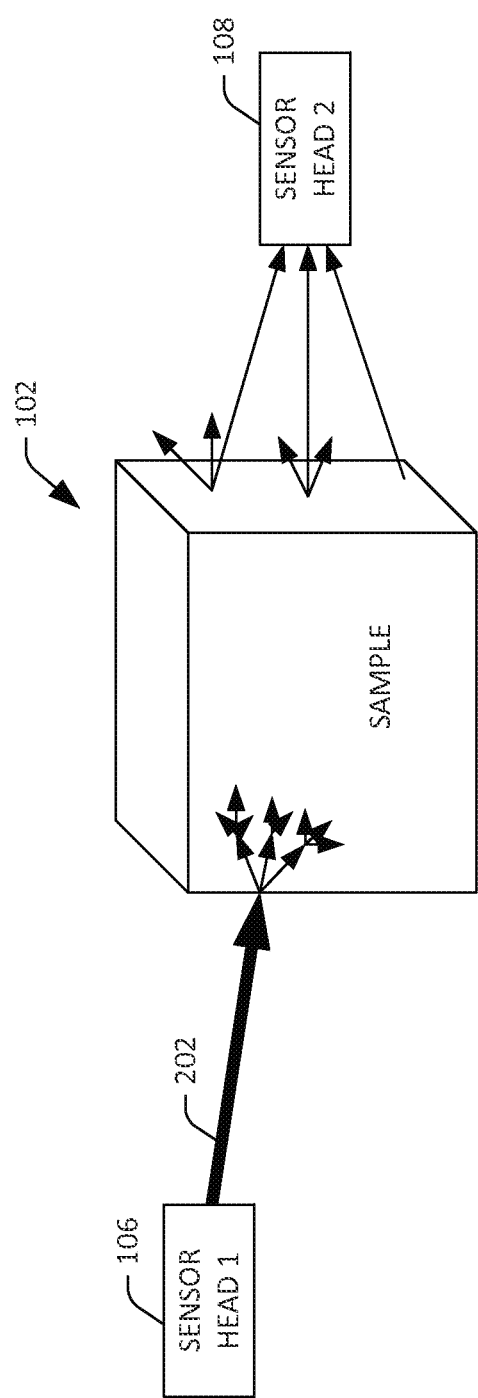
FIG. 2 illustrates a transillumination beam emitted from a sensor head of a diffuse optical tomography system that diffuses through a sample.

Now referring to FIG. 2, an exemplary depiction of the first sensor head 106 acting as the illuminator in the diffuse optical tomography system 100 and the second sensor had 108 acting as an observer is presented. The first optical emitter system 116 of the first sensor head 106 is configured to direct a transillumination beam 202 at a particular location on the sample 102. Upon impacting the sample 102, at least a portion of the transillumination beam 202 scatters volumetrically within the sample 102 and propagates diffusely. Some of the scattered light emerges from the side of the sample 102 that is within the field of view of the second sensor system 122 of the second sensor head 108, and enters an entrance pupil of the second sensor system 122. In addition to the second sensor system 122 outputting electrical signals that are indicative of transmission phase and amplitude of light captured in pixels of a focal plane array of the second sensor system 122, the sensor heads 110-114 may also act as observers, such that their respective sensor systems output electrical signals that are indicative of transmission phase and amplitude of light captured in pixels of their respective focal plane arrays. This technique of acquiring observations in parallel is vastly faster than the principally serial approach of lock-in amplifier demodulation that is the basis of conventional diffuse optical tomography systems.

Figure 3:
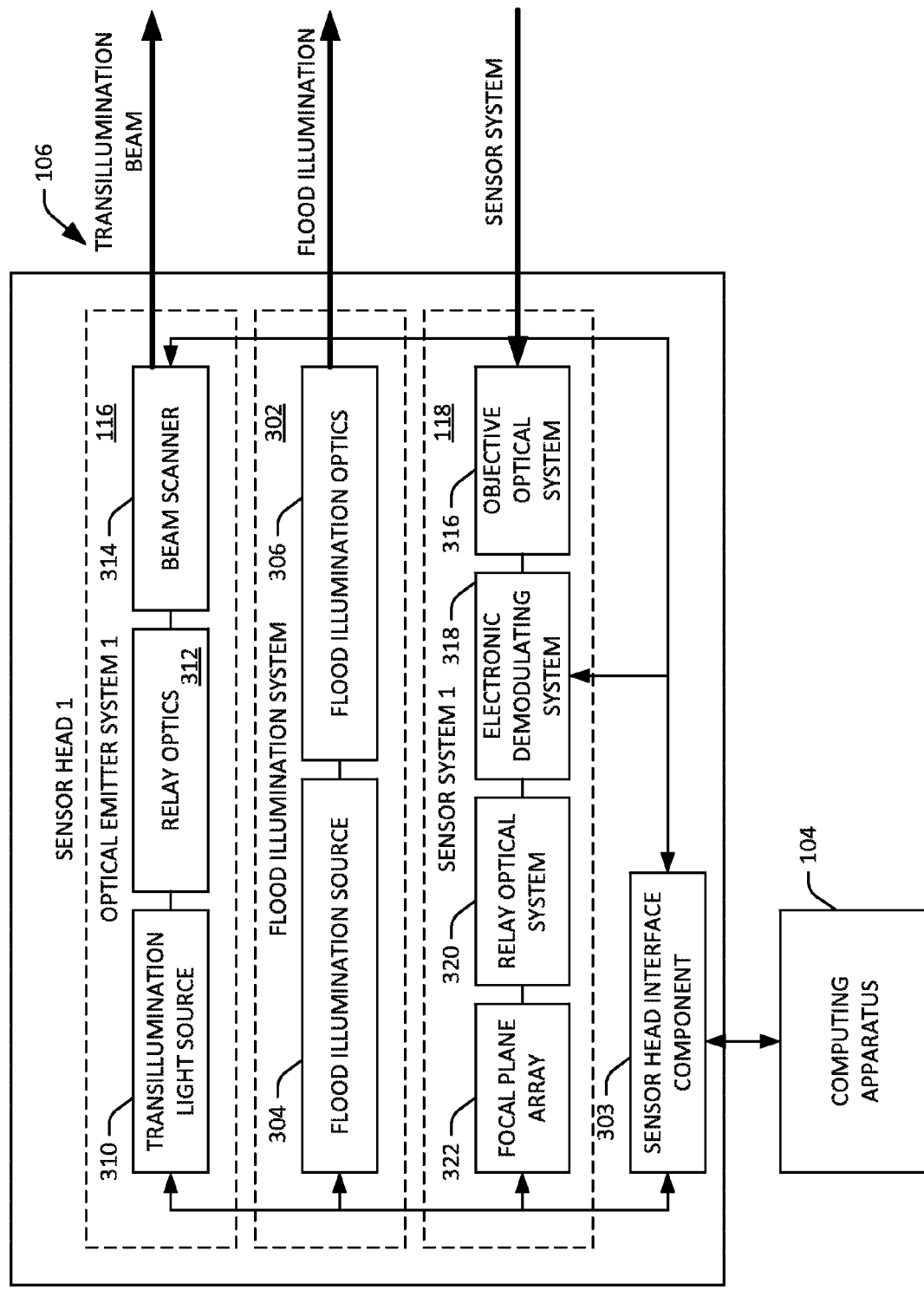
FIG. 3 is a functional block diagram of an exemplary sensor head that is employable in a diffuse optical tomography system.

With reference now to FIG. 3, in an exemplary embodiment, a functional block diagram of contents of the first sensor head 106 is illustrated. It is to be understood that other sensor heads in the diffuse optical tomography system 100 can include similar elements. As indicated above, the first sensor head 106 includes the first optical emitter system 116 and the first sensor system 118. The first sensor head 106 additionally optionally includes a flood illumination system 302 that is configured to output a flood illumination beam. Operation of the flood illumination system 302 and the optical emitter system 116 is mutually exclusive, such that when the flood illumination system 302 is active, the first optical emitter system 116 is inactive.

The first sensor head 106 further includes a sensor head interface component 303 that is in communication with the computing apparatus 104, the first optical emitter system 116, the flood illumination system 302, and the first sensor system 118. In general, the sensor head interface component 303 receives control signals from the computing apparatus 104 and controls operation of the first optical emitter system 116, the flood illumination system 302, and the first sensor system 118 based upon such control signals.

Details pertaining to the flood illumination system 302 are now set forth. The flood illumination system 302 comprises a flood illumination source 304 and flood illumination optics 306. The flood illumination source 304 can be or include a broadband light source, such as a xenon lamp, or can comprise an array of laser sources or light emitting diodes (e.g., arrays of monochromatic sources of various desired wavelengths). The flood illumination source 304 can be operated in a continuously emitting mode to illuminate the sample 102 or can be operated in a flash mode, whereby the sample 102 is illuminated by a flash of light. Duration of the flash can be between a microsecond and a millisecond. Flash illumination can be utilized in applications where it is desirable to maintain "eye safe" levels of illumination on the target (the sample 102). The flood illumination system 302 can further include flood illuminating optics 306 that receive light emitted from the flood illumination source 304. Flood illumination optics 306 can include, for example, a loss modulator that can comprise an electro-optic crystal disposed between a pair of crossed linear polarizers, wherein the electro-optic crystal is modulated at a particular sinusoidal frequency. The flood illumination optics 306 may further include spectral filters to resolve desired wavelengths. Generally, the flood illumination system 302 can be constructed and operated as described in U.S. Pat. Nos. 4,935,616, 7,420,656, 7,495,748 and/or 7,995,191, the entireties of which are incorporated herein by reference. When the flood illumination system 302 is active, the first sensor system 118 may likewise be active, and is configured to output topographical and photographical data in the manner described in the patents referenced above.

Additional detail pertaining to the first optical emitter system 116 is now set forth. The first optical emitter system 116 includes a transillumination light source 310, which may be, for instance, a laser or an array of lasers, a bulb, etc. The first optical emitter system 116 additionally includes relay optics 312 and a beam scanner 314, wherein the beam scanner 314 receives optics output by the relay optics 312. The computing apparatus 104 transmits control signals to the signal head interface component 303, wherein the control signals indicate a wavelength and amplitude of a beam to be emitted by the transillumination source 310 and a direction that the transillumination beam is to be output by the beam scanner 314. The sensor head interface component 303 can then transmit a signal to the transillumination light source 310 and the beam scanner 314, such that transillumination light source 310 emits a beam with a desired intensity and wavelength, and the beam scanner 314 directs the transillumination beam to a desired region on the sample 102.

The transillumination light source 310 can report its modulation timing to the sensor head interface component 303, which can communicate such information to the computing apparatus 104. The computing apparatus 104 may then control operation of other sensor heads in the system 100 based upon such information. The relay optics 312 adapt the beam emitted from the transillumination light source 310 for the beam scanner 314, which directs the beam toward the sample 102 as commanded by the computing apparatus 104. It can therefore be ascertained that the computing apparatus 104 and the sensor head interface component 303 can act in conjunction to control wavelengths of beams emitted by the transillumination light source 310 and position of beams emitted from the sensor head 106 onto the sample 102.

As indicated above, the transillumination light source 310 can comprise an array of selectable light sources, such as lasers tunable or operating at discrete spectral lines. Further, the transillumination light source 310 can be modulated by way of, for example, direct-current modulation (as is conventional for laser diodes), using electro-optic amplitude modulation or other suitable technique. Modulation, for instance, can occur at modulation frequencies in tens of megahertz to tens of gigahertz, depending upon a chemical or chemicals of interest. Beams from individual light sources in the transillumination light source 310 can be multiplexed into a single output beam by conventional methods of beam combining, such as prisms, diffraction gratings, and other techniques.

For purposes of ease of data analysis, the coherence length of each light source in the transillumination light source 310 can be short compared to a typical variation in path length through the volumetric scattering in the sample 102. Such approach may minimize speckle observed by observing sensor heads, which is pertinent for correct interpretation of the image data as being incoherent at the optical carrier frequency. For samples that are relatively highly scattering, such as breast tissue, typical path length variations may be on the scale of millimeters. Spectral widths on the order of 1 nm or more may then be sufficient. Since the absorption resonance of hemoglobin is on the order of 50 nm wide, several independent operating wavelengths of a few nanometers of spectral width may be practical. Such spectral width is typical of laser diodes.

When applied to mapping other biomolecules, or when applied to optical diffuse material whose chemical structure may be isolated by distinctive and typically narrow spectral absorption resonances in the infrared, it may not be possible for the coherence length of the light source to be short enough to avoid speckle and yet long enough to be well within a spectral absorption line, or light sources of suitably short coherence length may be difficult to obtain. In such a case, the transillumination light source 310 may additionally utilize an optical frequency dithering device, such as an electro-optic phase modulator, to suppress speckle.

Additional detail pertaining to structure and operation of the first sensor system 118 is now set forth. When the first sensor system 118 is active, the first optical emitter system 116 is inactive. When the first sensor system 118 is active (and the flood illumination system 302 is inactive), the first sensor system 118 can be generally configured to detect light radiating from the sample 102. The first sensor system 118 includes an objective optical system 316, which collects a portion of a transillumination beam emitted from an illuminator sensor head in the diffuse optical tomography system 100. An electronic demodulating system 318 receives light captured by the objective optical system 316, and demodulates the light in accordance with a known wavelength or wavelengths of the transillumination beam emitted from the illuminator sensor head (e.g., one of the sensor heads 108-114). A relay optical system 320 receives the demodulated light and passes such light to a focal plane array 322. Signals output by the focal plane array 322 are indicative of, at each pixel in the focal plane array 322, transmission phase and amplitude of light radiating from the sample 102 in the field of view of the sensor system 118. These electrical signals can be read from the focal plane array 322 by the sensor head interface component 303 and transmitted to the computing apparatus 104, which can generate a volumetric image of the sample 102 based at least in part upon such electrical signals.

Figure 4:
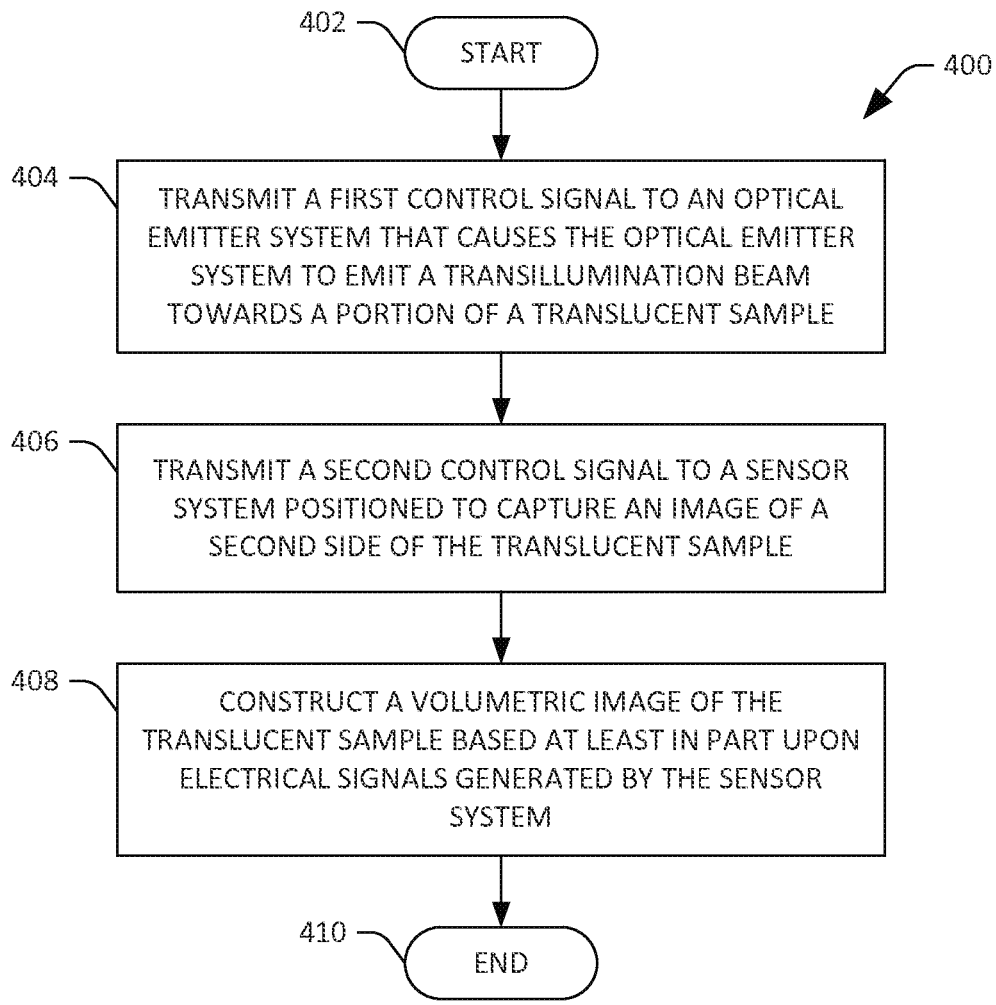
FIG. 4 is a flow diagram illustrating an exemplary methodology for constructing a volumetric image of a sample.
Figure 5:
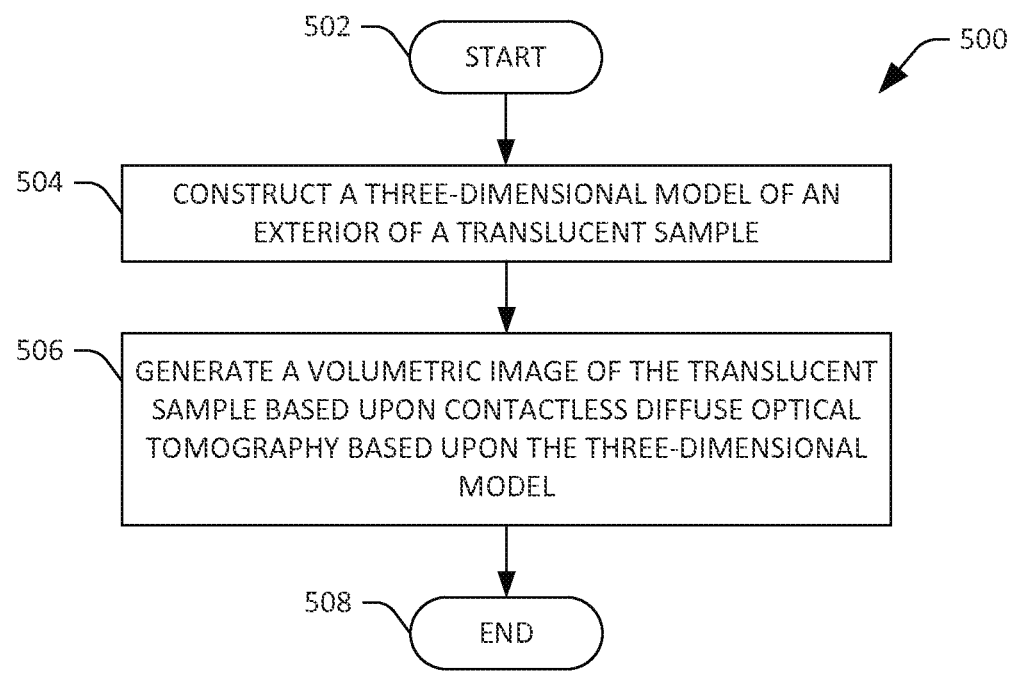
FIG. 5 is a flow diagram illustrating an exemplary methodology for generating a volumetric image of a sample based upon contactless diffuse optical tomography.

FIGS. 4-5 illustrate exemplary methodologies relating to diffuse optical tomography. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 4, an exemplary methodology 400 for constructing a volumetric image of a sample (e.g., translucent, semi-clear, or transparent sample) by way of diffuse optical tomography is illustrated. The methodology 400 starts at 402, and at 404, a first control signal is transmitted to an optical emitter system that causes the optical emitter system to emit a transillumination beam towards a portion of a first side of the sample. The transillumination beam may have a particular wavelength or may have a plurality of wavelengths. Further, the transillumination beam is an intensity-modulated transillumination beam.

At 406, a second control signal is transmitted to a sensor system that is positioned to capture measurements pertaining to a second side of the sample (different from the first side), wherein the second control signal causes the sensor system to generate images of the sample. The images are indicative of transmission phase and amplitude of light radiating from the sample in a field of view of the sensor system. For example, the sensor system may include a focal plane array that is configured to generate measurements for a plurality of pixels in the field of view of the sensor system. Thus, the sensor system is configured to generate electrical signals that are indicative of respective transmission phases and respective amplitudes of portions of the transillumination beam that exit the second side of the sample.

At 408, a volumetric image of the sample is constructed based at least in part upon the electrical signal generated by the sensor system. The methodology 400 completes at 410.

With reference now to FIG. 5, an exemplary methodology 500 that facilitates generating a volumetric image of a sample (e.g., translucent, semi-clear, or transparent sample) is illustrated. The methodology 500 starts at 502, and at 504, a three-dimensional model of an exterior of a sample is constructed. The three-dimensional model can be constructed by causing flood illumination systems to emit intensity-modulated light beams that are reflected from a surface of the sample, thereby allowing for electrical signals to be generated at pixels of a focal plane array that are indicative of distance between the focal plane array and the sample at each pixel. By generating such data at a plurality of different sides of the sample, a three-dimensional model of the sample can be constructed.

At 506, a volumetric image of the sample is generated by way of contactless diffuse optical tomography and based upon the three-dimensional model constructed at 504. For instance, the three-dimensional model can provide physical boundaries for measurements generated by the diffuse optical tomography system. The methodology 500 completes at 508.

Figure 6:
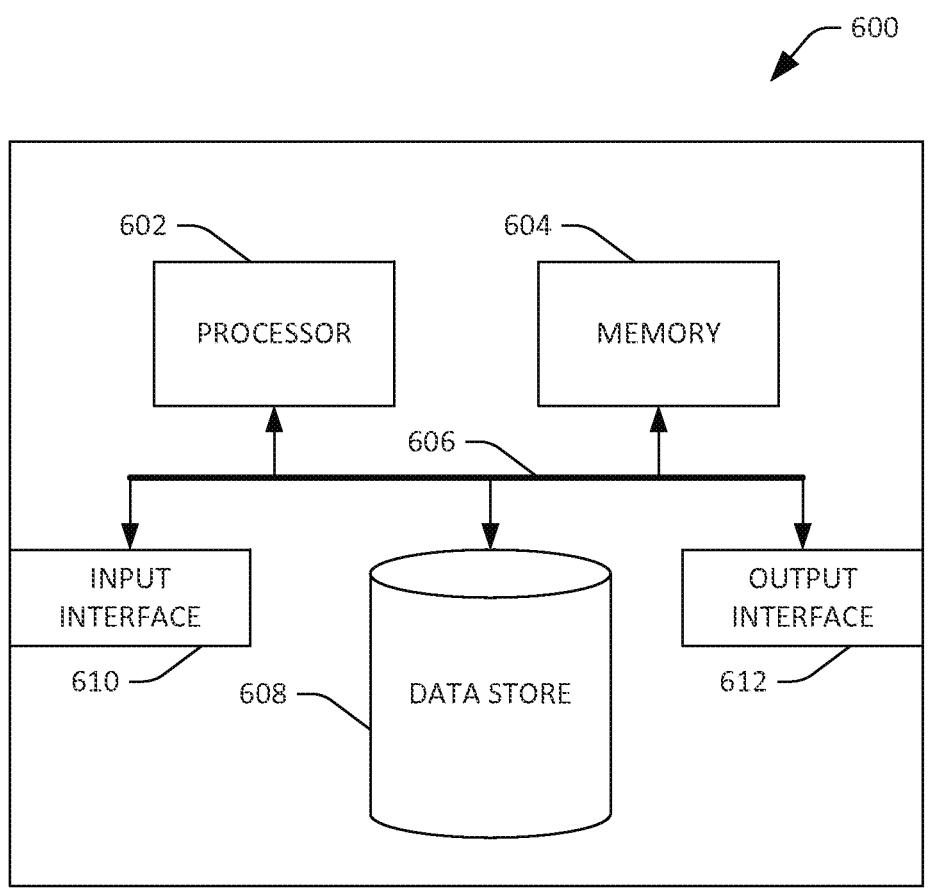
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that generates volumetric images of samples. Therefore, for instance, the computing device 600 can be used in a diffuse optical tomography mammography system. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store images, absorption frequencies, etc.

The computing device 600 additionally includes a data store 608 that is accessible by the processor 602 by way of the system bus 606. The data store 608 may include executable instructions, images, etc. The computing device 600 also includes an input interface 610 that allows external devices to communicate with the computing device 600. For instance, the input interface 610 may be used to receive data output by the sensor heads 106-114. The computing device 600 also includes an output interface 612 that interfaces the computing device 600 with one or more external devices. For example, the computing device 600 can transmit control signals to the sensor heads by way of the output interface 612.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber-optic cable, twisted pair, digital subscriber line (DSL), or wireless technologies such as infrared, radio, and microwave, then the coaxial cable, fiber-optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system for generating a volumetric image of a sample, the system comprising:
   an optical emitter system that emits an intensity-modulated first transillumination beam towards a portion of the sample;
   a plurality of sensor systems comprising sensors each having a plurality of individual pixels and positioned at different respective locations about the sample, the plurality of sensor systems configured to demodulate light from the intensity-modulated first transillumination beam emerging from the sample within a field of view of each sensor and directed toward the sensors, the demodulation occurring in parallel among the intensity-modulated first transillumination beam corresponding to the plurality of pixels of each sensor, wherein the individual pixels are exposed to a demodulated transillumination beam instead of the intensity-modulated first transillumination beam, and wherein the individual pixels detect, in parallel, demodulated respective portions of the intensity-modulated first transillumination beams that exit the sample in the fields of view of the respective sensor systems, the plurality of sensor systems further configured to output respective electrical signals based on the demodulated transillumination beam instead of the intensity-modulated first transillumination beam, wherein the respective electrical signals include volumetric information obtained from the demodulation; and a computing apparatus in communication with the plurality of sensor systems, the computing apparatus receives the electrical signals output by the respective sensor systems and generates the volumetric image of the sample based upon the electrical signals.

2. The system of claim 1, the sample being human tissue.

3. The system of claim 2, the human tissue being breast tissue.

4. The system of claim 1, a first sensor head comprising the optical emitter system, the first sensor head further comprising a first sensor system, the first sensor head positioned relative to the sample such that the first sensor system is configured to capture images of a first side of the sample.

5. The system of claim 4, wherein the computing apparatus comprises a control component that causes the computing apparatus to transmit a first control signal to the first sensor head, the first control signal causing the first sensor system to fail to capture images of the first side of the sample when the optical emitter system emits the first transillumination beam towards the portion of the sample.

6. The system of claim 5, a plurality of sensor heads respectively comprising the plurality of sensor systems, the plurality of sensors heads further comprising a respective plurality of optical emitter systems that are positioned to emit a respective plurality of transillumination beams towards a respective plurality of portions of the sample.

7. The system of claim 6, wherein the control component causes the computing apparatus to transmit a respective plurality of control signals to the plurality of sensor systems, the respective plurality of control signals causing the respective plurality of optical emitter systems to fail to emit transillumination beams when the optical emitter system emits the first transillumination beam.

8. The system of claim 7, the plurality of sensor heads comprising at least three sensor heads.

9. The system of claim 1, the computing apparatus configured to generate a three-dimensional model of an exterior of the sample, the volumetric image based upon the three-dimensional model of the exterior of the sample.

10. The system of claim 1, each individual pixel of the plurality of individual pixels comprising a respective plurality of focal plane arrays.

11. The system of claim 1, the plurality of sensor systems failing to contact the sample.

* * * * *